US011450062B2

(12) United States Patent
Park et al.

(10) Patent No.: US 11,450,062 B2
(45) Date of Patent: Sep. 20, 2022

(54) METHOD AND APPARATUS FOR GENERATING 3-D MOLECULAR IMAGE BASED ON LABEL-FREE METHOD USING 3-D REFRACTIVE INDEX IMAGE AND DEEP LEARNING

(71) Applicants: Tomocube, Inc., Daejeon (KR); Korea Advanced Institute of Science and Technology, Daejeon (KR)

(72) Inventors: YongKeun Park, Daejeon (KR); Weisun Park, Daejeon (KR); Youngju Jo, Daejeon (KR); Hyunseok Min, Daejeon (KR); Hyungjoo Cho, Daejeon (KR)

(73) Assignees: Tomocube, Inc., Daejeon (KR); Korea Advanced Institute of Science and Technology, Daejeon (KR)

( * ) Notice: Subject to any disclaimer, the term of this patent is extended or adjusted under 35 U.S.C. 154(b) by 167 days.

(21) Appl. No.: 16/823,453

(22) Filed: Mar. 19, 2020

(65) Prior Publication Data

US 2021/0134054 A1 May 6, 2021

(30) Foreign Application Priority Data

Nov. 5, 2019 (KR) .......................... 10-2019-0139992

(51) Int. Cl.
*G06K 9/00* (2022.01)
*G06T 17/00* (2006.01)
(Continued)

(52) U.S. Cl.
CPC ................ *G06T 17/00* (2013.01); *C12Q 1/02* (2013.01); *G01N 21/6428* (2013.01);
(Continued)

(58) Field of Classification Search
None
See application file for complete search history.

(56) References Cited

U.S. PATENT DOCUMENTS

| 2017/0357084 A1* | 12/2017 | Park | G01N 21/4133 |
| 2019/0251330 A1* | 8/2019 | Cotte | G06K 9/0014 |
| 2021/0142170 A1* | 5/2021 | Ozcan | G02B 5/1866 |

FOREIGN PATENT DOCUMENTS

| JP | H09281405 A | 10/1997 |
| JP | 2009014939 A | 1/2009 |

(Continued)

OTHER PUBLICATIONS

Emil Wolf, "Three-Dimensional Structure Determination of Semi-Transparent Objects From Holographic Data," Optics Communications, Sep./Oct. 1969, pp. 153-156, vol. 1, No. 4.

(Continued)

*Primary Examiner* — Wei Wen Yang
(74) *Attorney, Agent, or Firm* — McCormick, Paulding & Huber PLLC

(57) ABSTRACT

Disclosed are a method and apparatus for generating a three-dimensional (3-D) molecular image based on a label-free method using a 3-D refractive index image and deep learning. The apparatus for generating a 3-D molecular image based on a label-free method using a 3-D refractive index image and deep learning may include a 3-D refractive index cell image measurement unit configured to measure a 3-D refractive index image of a cell to be monitored and a 3-D refractive index and fluorescence molecule staining image conversion unit configured to input a measured value of the 3-D refractive index image to a deep learning algorithm and to output a 3-D fluorescence molecule staining cell image of the cell.

10 Claims, 21 Drawing Sheets

(51) Int. Cl.
    *C12Q 1/02*     (2006.01)
    *G01N 21/64*     (2006.01)
    *G06T 7/00*     (2017.01)

(52) U.S. Cl.
    CPC .... *G06T 7/0012* (2013.01); *G01N 2021/6439* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01)

(56) References Cited

FOREIGN PATENT DOCUMENTS

| | | |
|---|---|---|
| JP | 2018206260 A | 12/2018 |
| KR | 10-2017-0140473 A | 12/2017 |
| KR | 10-1977067 B1 | 5/2019 |
| WO | 2019/032723 A1 | 2/2019 |
| WO | 2019060141 A1 | 3/2019 |
| WO | 2019/191697 A1 | 10/2019 |

OTHER PUBLICATIONS

Kyoohyun Kim et al., "Optical diffraction tomography techniques for the study of cell pathophysiology," J of Biomedical Photonics & Eng 2(2), Jun. 14, 2016.
KyeoReh Lee et al., "Quantitative Phase Imaging Techniques for the Study of Cell Pathophysiology From Principles to Applications," Sensors 2013, pp. 4170-4191.
Eric M. Christiansen, et al., "In Silico Labeling: Predicting Fluorescent Labels in Unlabeled Images", Cell, vol. 173, No. 3, Apr. 19, 2018, pp. 792-803.
Chawin Ounkomol, et al., "Label-free prediction of three-dimensional fluorescence images from transmitted light microscopy", bioRxiv, Mar. 27, 2018, doi: http://dx.doi.org/10.1101/289504.
Seyed Raein Hashemi, et al., "Asymmetric Loss Functions and Deep Densely Connected Networks for Highly Imbalanced Medical Image Segmentation: Application to Multiple Sclerosis Lesion Detection", IEEE Access, arxiv.org, Cornell University Library, Mar. 28, 2018.
Joseph Y. Cheng, et al., "Highly Scalable Image Reconstruction using Deep Neural Networks with Bandpass Filtering", arxiv.org, Cornell University Library, May 8, 2018.
Extended European Search Report for European Patent Application No. 20163081.1 dated Sep. 2, 2020.
Minhee Kang, et al., "Rapid and label-free identification of individual bacterial pathogens exploiting three-dimensional quantitative phase imaging and deep learning", bioRxiv, Apr. 3, 2019, doi: http://dx.doi.org/10.1101/596486.

* cited by examiner

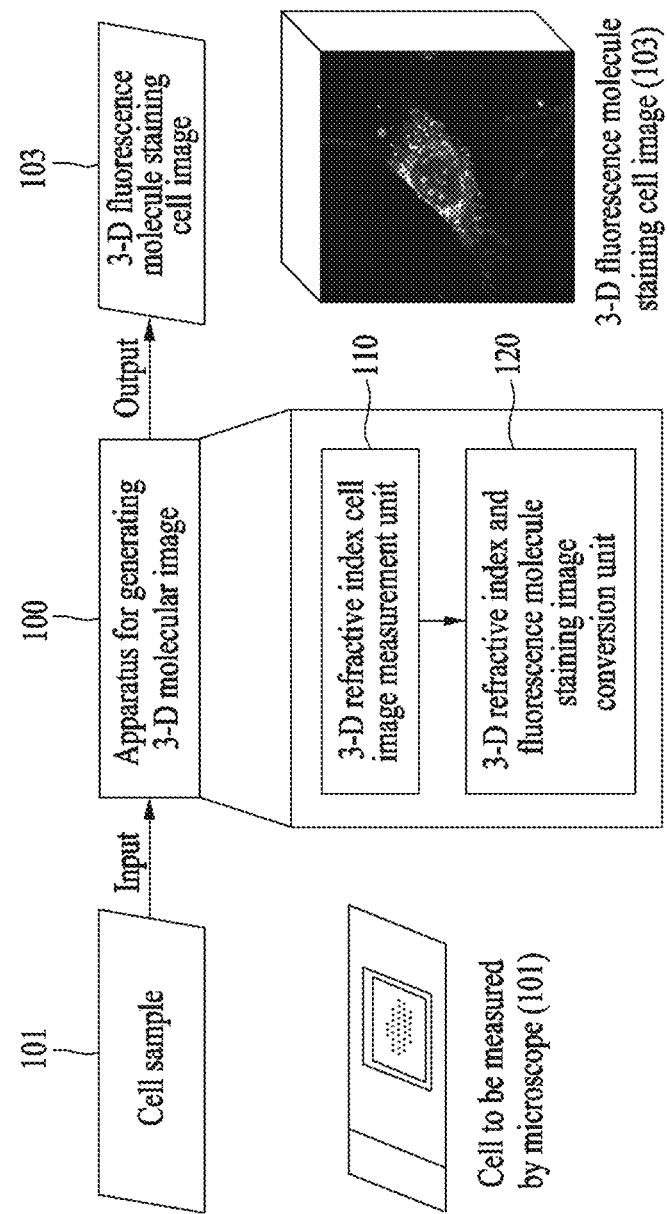

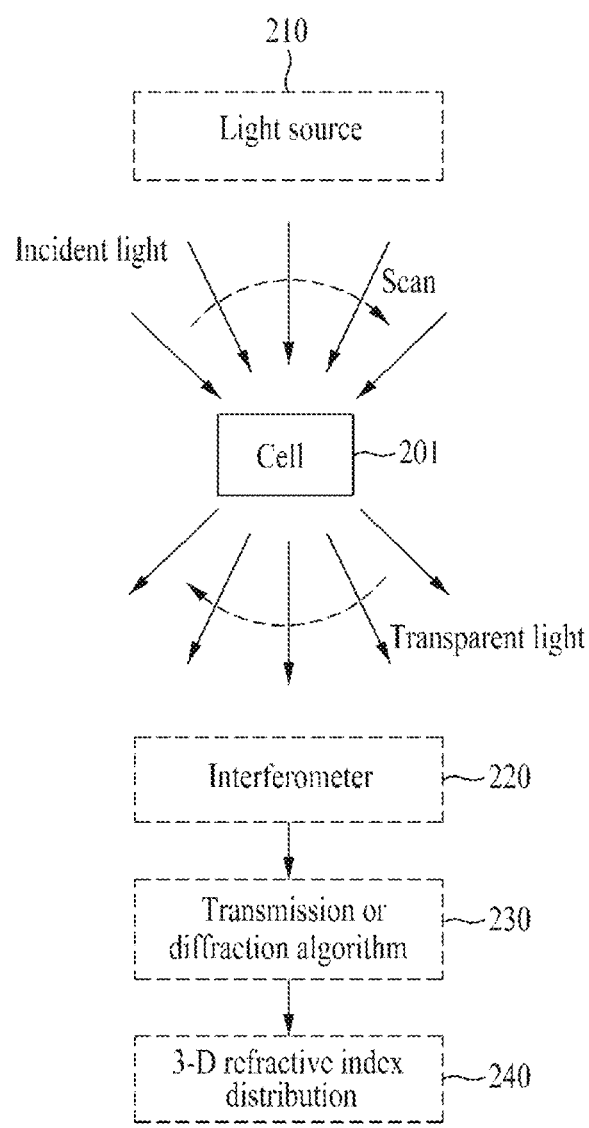

Reconstructed 3-D fluorescence
molecule staining cell image

Reconstructed 3-D fluorescence
molecule staining cell image

METHOD AND APPARATUS FOR GENERATING 3-D MOLECULAR IMAGE BASED ON LABEL-FREE METHOD USING 3-D REFRACTIVE INDEX IMAGE AND DEEP LEARNING

CROSS REFERENCE TO RELATED APPLICATION

This application is based on and claims priority under 35 U.S.C. 119 to Korean Patent Application No. 10-2019-0139992, filed on Nov. 5, 2019, in the Korean Intellectual Property Office, the disclosures of which is herein incorporated by reference in their entireties.

BACKGROUND OF THE INVENTION

1. Technical Field

The following embodiments relate to a method and apparatus for generating a three-dimensional (3-D) molecular image based on a label-free method and, more particularly, to a method and apparatus for generating a 3-D molecular image based on a label-free method using a 3-D refractive index image and deep learning.

2. Description of the Related Art

Today, for the monitoring and measurement of a specific substance/structure in a cell/tissue using a microscope, in general, a method of monitoring or measuring molecules emitted from a tissue or cell on which the molecules are floated or labeled with a molecular material using a molecular microscope is used.

Accordingly, there are problems in that time and costs are necessary for a dyeing process, the deformation of a cell is inevitable due to the dyeing process, and quality of a corresponding image is not constant in using the quality for the dyeing process and the state of a sample.

It is also difficult to track and monitor a sample on which a fluorescence molecule staining process has been performed or to monitor the sample again for a long time because it is difficult to remove fluorescence molecule staining from the sample. Due to such problems, the application of a molecular microscope is limited in the monitoring of a cell/tissue in a new field.

Prior Art Document

[Non-patent document]
(Non-patent document 1) Kim, K., et al. (2016). "Optical diffraction tomography techniques for the study of cell pathophysiology." arXiv preprint arXiv:1603.00592.
(Non-patent document 2) Lee, K., et al. (2013). "Quantitative phase imaging techniques for the study of cell pathophysiology: from principles to applications." Sensors 13(4): 4170-4191.
(Non-patent document 3) Wolf, E. (1969). "Three-dimensional structure determination of semi-transparent objects from holographic data." Optics Communications 1(4): 153-156.

SUMMARY OF THE INVENTION

Embodiments describe a method and apparatus for generating a 3-D molecular image based on a label-free method using a 3-D refractive index image and deep learning. More specifically, there is provided a technology for rapidly generating a molecular microscope image using a 3-D refractive index image of a cell and a deep learning algorithm without a process, such as dyeing or labeling.

Embodiments provide a method and apparatus for generating a 3-D molecular image based on a label-free method using a 3-D refractive index image and deep learning, wherein a 3-D molecular microscope image is generated by applying a deep learning algorithm in order to measure the morphologic features of a cell using a 3-D refractive index microscope without dyeing or labeling and to predict a molecular image for monitoring the physical/chemical characteristics of the cell based on the morphologic features.

In an embodiment, an apparatus for generating a three-dimensional (3-D) molecular image based on a label-free method using a 3-D refractive index image and deep learning may include a 3-D refractive index cell image measurement unit configured to measure a 3-D refractive index image of a cell to be monitored, and a 3-D refractive index and fluorescence molecule staining image conversion unit configured to input a measured value of the 3-D refractive index image to a deep learning algorithm and to output a 3-D fluorescence molecule staining cell image of the cell.

The 3-D refractive index cell image measurement unit may capture the 3-D refractive index image in a form in which the cell to be monitored is placed or painted on a slide.

The 3-D refractive index cell image measurement unit may include a 3-D image patch photographing unit configured to capture a 3-D refractive index image capable of being captured at a time when a monitoring area of the cell is greater than an area capable of being photographed at a time, and an image patch combination unit configured to generate a 3-D refractive index slide image by connecting the 3-D refractive index images each captured at a time.

The 3-D refractive index and fluorescence molecule staining image conversion unit may include a 3-D patch extraction unit configured to generate a 3-D refractive index image patch of the cell, a 3-D refractive index and fluorescence molecule staining patch conversion unit configured to convert the 3-D refractive index image patch into a 3-D molecular image patch based on the deep learning algorithm, and a molecule patch combination unit configured to merge the converted 3-D molecular image patches into a single image.

The 3-D patch extraction unit may include an image padding unit configured to perform a padding process in order to prevent a loss of outskirt area values of an image, a cell area extraction unit configured to extract a cell area from an image on which the padding process has been performed, and a 3-D refractive index patch sampling unit configured to generate the 3-D refractive index image patch of the cell by sampling a patch in the cell area of the padded image.

The 3-D refractive index and fluorescence molecule staining patch conversion unit may convert the 3-D refractive index image patch of each cell into the 3-D molecular image patch using a convolutional neural network (CNN) trained based on 3-D refractive index information.

The molecule patch combination unit may multiply and add a linear or non-linear weight according to the distance from the middle of the patch in order to guarantee a continuity of an image reconstructed for an overlapped area, may remove a padding area, and may finally generate the 3-D fluorescence molecule staining cell image of the cell for one molecular label.

The 3-D refractive index and fluorescence molecule staining image conversion unit may include a 3-D refractive index and fluorescence molecule staining image conversion model generation unit configured to measure the preset number of samples or more for each molecular label and to construct a 3-D refractive index and fluorescence molecule staining image conversion model using the deep learning algorithm. The 3-D fluorescence molecule staining cell image of the cell may be generated by measuring a 3-D refractive index image corresponding to a cell having a specific molecular label through the 3-D refractive index and fluorescence molecule staining image conversion model.

In another embodiment, a method of generating a three-dimensional (3-D) molecular image based on a label-free method using a 3-D refractive index image and deep learning may include measuring a 3-D refractive index image of a cell to be monitored and inputting a measured value of the 3-D refractive index image to a deep learning algorithm and outputting a 3-D fluorescence molecule staining cell image of the cell.

Outputting the 3-D fluorescence molecule staining cell image of the cell may include measuring a preset number of samples or more for each molecular label and constructing a 3-D refractive index and fluorescence molecule staining image conversion model using the deep learning algorithm. The 3-D fluorescence molecule staining cell image of the cell may be generated by measuring a 3-D refractive index image corresponding to a cell having a specific molecular label through the 3-D refractive index and fluorescence molecule staining image conversion model.

BRIEF DESCRIPTION OF THE DRAWINGS

FIG. 1 is a block diagram for describing an apparatus for generating a 3-D molecular image based on a label-free method using a 3-D refractive index image and deep learning according to an embodiment.

FIG. 2A is a diagram for describing a method of measuring a 3-D refractive index of a cell using an incident light rotation method according to an embodiment.

DETAILED DESCRIPTION

Figure 2B:
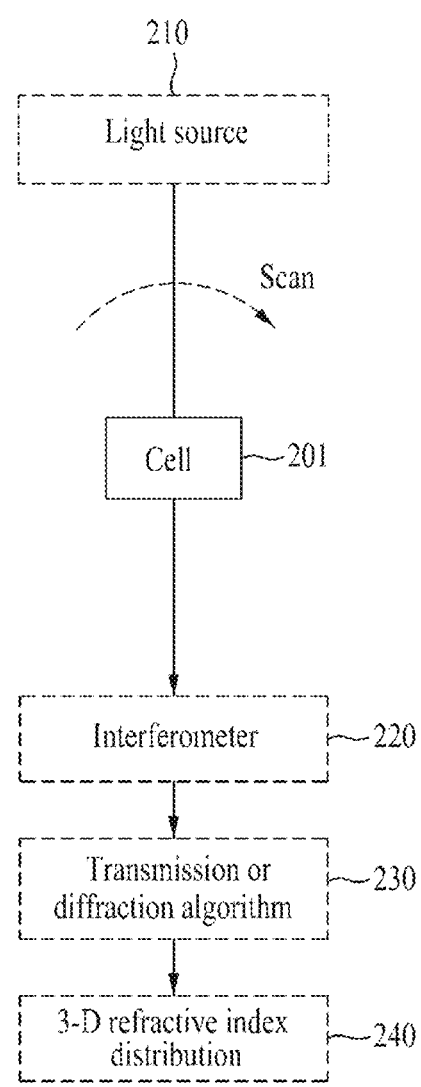
FIG. 2B is a diagram for describing a method of measuring a 3-D refractive index of a cell using a cell rotation method according to an embodiment.

Hereinafter, embodiments of the disclosure are described in detail with reference to the accompanying drawings. However, the described embodiments may be modified in various other forms, and the scope of the disclosure is not restricted by the following embodiments. Furthermore, the embodiments of the disclosure are provided to fully describe the disclosure to a person having ordinary knowledge in the art to which the disclosure pertains. The shapes, sizes, etc. of elements in the drawings may be exaggerated for a clear description.

In the analysis of a sample using a microscope, in a conventional technology, a molecular microscope is chiefly used to monitor and measure a specific substance/structure within the sample. Such a molecular microscope is equipment for monitoring a micro structure and physical and chemical characteristics based on molecules emitted from a tissue or cell that naturally shows molecules or that is labeled with molecular materials. However, the microscope has problems in that a label process using a molecular material is essential and accurate characteristics of a live cell are not obtained because a label process affects the cell. For example, the results of research in which if labeling, such as dyeing, is performed in order to monitor one actin of subcellular organelles of a cell, the structure of the cell is changed were published. For this reason, the inborn structure and information of a cell need to be monitored without labeling.

The following embodiments provide a method of rapidly generating a molecular microscope image using the three-dimensional (3-D) refractive index measurement of a cell and a deep learning algorithm without a process, such as dyeing or labeling using a molecular material. That is, in the embodiments, a 3-D molecular microscope image is generated by applying a deep learning algorithm in order to measure the morphologic features and physical characteristics of a cell using a 3-D refractive index microscope without dyeing or labeling and to predict a molecular label for monitoring the physical-chemical characteristics of the cell based on the measured morphologic features and physical characteristics. In this case, the molecular image may include an organic dye (H&E staining, Wright staining), immunological staining, fluorescence molecule staining, and fluorescence protein expression.

A 3-D refractive index distribution within a cell is closely related to the configuration and shape of subcellular organelles within the cell. Furthermore, a refractive index value itself is proportional to a concentration of proteins, that is, a major constituent element of a cell. Accordingly, to measure 3-D refractive index information of a cell includes incorporating biochemical characteristics information in addition to the cell and the morphological characteristics of subcellular organelles within the cell. Accordingly, if a 3-D refractive index distribution is used, characteristics related to a molecular label for monitoring specific subcellular organelles can be extracted. A 3-D molecular image can be reconstructed and provided based on such characteristics.

As a result of research of an example in which the above object has been incorporated, an accurate molecular image can be generated simply and rapidly as a result of applying a deep learning algorithm as a conversion algorithm for measuring a 3-D refractive index of a cell and using a corresponding measurement value as input.

FIG. 1 is a block diagram for describing an apparatus for generating a 3-D molecular image based on a label-free method using a 3-D refractive index image and deep learning according to an embodiment.

Referring to FIG. 1, an apparatus 100 for generating a 3-D molecular image based on a label-free method using a 3-D refractive index image and deep learning according to an embodiment may receive a monitoring sample to be monitored as input, and may output a 3-D molecular image of a corresponding cell.

The apparatus 100 for generating a 3-D molecular image based on a label-free method using a 3-D refractive index image and deep learning according to an embodiment may include a 3-D refractive index cell image measurement unit 110 and a 3-D refractive index and fluorescence molecule staining image conversion unit 120.

The 3-D refractive index cell image measurement unit 110 may measure a 3-D refractive index image of a cell 101 to be monitored. For example, the 3-D refractive index cell image measurement unit 110 may capture a 3-D refractive index image in the state in which the cell 101 to be monitored is placed or painted on the slide.

If a monitoring area of the cell 101 is greater than an area which may be photographed at a time, the 3-D refractive index cell image measurement unit 110 may capture a 3-D refractive index image which may be captured at a time, and may generate a 3-D refractive index slide image by connecting the 3-D refractive index images each captured at a time.

The 3-D refractive index cell image measurement unit 110 may be configured with a light source, an interferometer, and a measurement unit.

The light source may have light incident on a cell. For example, a laser may be used as the light source. The light source may radiate a laser beam to a sample, such as the cell 101 to be measured. In this case, the cell 101 indicates a target to be measured. A single wavelength laser may be used as the light source. Furthermore, the light source may be used to distinguish between more pieces of information of cells by measuring 3-D refractive indices in wavelengths using several wavelength lasers.

The interferometer may obtain multiple 2-D holograms by measuring transmission light diffracted from the cell 101 after light from a light source is incident on the cell 101. In this case, the interferometer is a measuring device using an interference phenomenon of light, and is an apparatus for dividing pieces of light from the same light source into two parts or more so that there is a difference between the travel paths of the light and monitoring an interference phenomenon occurring when the pieces of light are met.

The measurement unit may measure a 3-D refractive index distribution of the cell 101 using multiple 2-D holograms obtained from the interferometer. For example, a camera, that is, a photographing device for capturing an image, may be used as the measurement unit.

The 3-D refractive index cell image measurement unit 110 may measure a 3-D refractive index distribution of a cell through at least one optical measurement of an optical diffraction tomography method and an optical projection tomography method. The 3-D refractive index cell image measurement unit 110 may measure a 3-D refractive index distribution of a cell using multiple 2-D holograms measured by the interferometer by rotating the angle of light incident on the cell 101. Furthermore, the 3-D refractive index cell image measurement unit 110 may measure a 3-D refractive index distribution of a cell using multiple 2-D holograms measured by the interferometer by directly rotating the cell 101.

Furthermore, the 3-D refractive index and fluorescence molecule staining image conversion unit 120 may input a measured value of a 3-D refractive index image to a deep learning algorithm, and may output a 3-D fluorescence molecule staining cell image 103 of the cell 101.

The 3-D refractive index and fluorescence molecule staining image conversion unit 120 may generate a 3-D refractive index image patch 102a of the cell 101, may convert the 3-D refractive index image patch 102a into a 3-D fluorescence molecule staining image patch 103a based on a deep learning algorithm, and may merge the converted 3-D fluorescence molecule staining image patches 103a into a single image. In this case, the 3-D refractive index and fluorescence molecule staining image conversion unit 120 may convert the 3-D refractive index image patch 102a of each cell 101 into the 3-D fluorescence molecule staining image patch 103a using a convolutional neural network (CNN) trained based on 3-D refractive index information.

The 3-D refractive index and fluorescence molecule staining image conversion unit 120 may include a 3-D refractive index and fluorescence molecule staining image conversion model generation unit 124. The 3-D refractive index and fluorescence molecule staining image conversion model generation unit 124 may measure the preset number of samples or more for each molecular label, and may construct a 3-D refractive index and fluorescence molecule staining image conversion model 122a using a deep learning algorithm. Accordingly, the 3-D refractive index and fluorescence molecule staining image conversion unit 120 may generate a 3-D fluorescence molecule staining cell image 103 of the cell 101 by measuring a 3-D refractive index image corresponding to a cell having a specific molecular label through the 3-D refractive index and fluorescence molecule staining image conversion model 122a.

The measurement of a 3-D refractive index image of a cell, that is, a target sample to be measured, is described below.

FIG. 2A is a diagram for describing a method of measuring a 3-D refractive index of a cell using an incident light rotation method according to an embodiment. Furthermore, FIG. 2B is a diagram for describing a method of measuring a 3-D refractive index of a cell using a cell rotation method according to an embodiment.

Referring to FIGS. 2A and 2B, various measurement optical implementations are illustrated as much as possible. All objects have their refractive index distributions. The refractive index is a unique optical physical quantity of a substance itself that describes how much is the speed decelerated when light passes through the substance. In order to measure a 3-D refractive index of a cell 201, an optical diffraction tomography method or an optical projection tomography method (or tomography phase microscopy or 3D digital holographic microscopy) may be used (Non-patent document 1, 2).

As illustrated in FIG. 2A, the optical diffraction tomography method and the optical projection tomography method may use the same optical implementation (Non-patent document 3). Light emitted from a coherent light source 210 may be incident on the cell 201. The hologram of transmission light diffracted by the cell 201 may be measured using an interferometer 220. In this case, a 3-D refractive index distribution of the cell 201 may be measured (240) using several sheets of two-dimensional (2-D) holograms measured while the angle of light incident on the cell 201 is rotated (or scanned). In this case, a difference between the diffraction tomography method and the projection tomography method lies in a restoration algorithm 230 in which the presence or absence of diffraction of light in a sample is taken into consideration.

Referring to FIG. 2B, instead of rotating incident light in a method of measuring a 3-D refractive index distribution of the cell 201 using the incident light rotation method described with reference to FIG. 2a, a 3-D refractive index distribution may be measured (240) by directly rotating the cell 201.

A method of measuring the cell 201 may include a form in which cells 201 having a low concentration have been placed on (in vitro) slide glass, a form in which cells 201 having a high concentration have been placed on (in vitro) slide glass to form a single or several layers, a tissue slide form in which a living tissue slide has been cut in thickness between 5 micrometers and 50 micrometer, and a form in which cells pass through a microfluidic channel for high-throughput screening in vitro.

Figure 3:
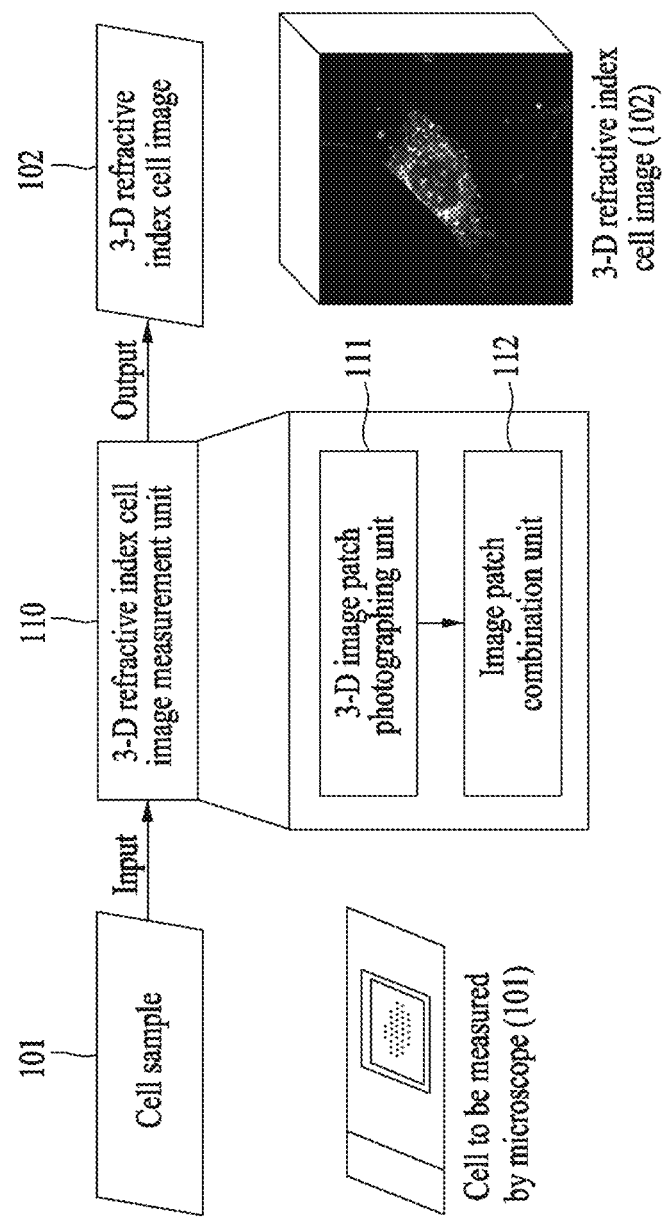
FIG. 3 is a diagram for describing a 3-D refractive index cell image measurement unit according to an embodiment.

FIG. 3 is a diagram for describing the 3-D refractive index cell image measurement unit according to an embodiment.

A 3-D refractive index image is captured in a form in which a cell to be monitored is placed or painted on a slide. As illustrated in FIG. 3, if a monitoring area of a cell is greater than an area that may be photographed at a time, a 3-D refractive index slide image may be generated by connecting 3-D images each captured at a time.

More specifically, the 3-D refractive index cell image measurement unit 110 may include a 3-D image patch photographing unit 111 and an image patch combination unit 112.

The 3-D image patch photographing unit 111 may capture a 3-D refractive index image which may be captured at a time if an area which may be photographed at a time is greater than a monitoring area of a cell.

Furthermore, the image patch combination unit 112 may generate a 3-D refractive index slide image by connecting 3-D refractive index images each captured at a time.

Figure 4:
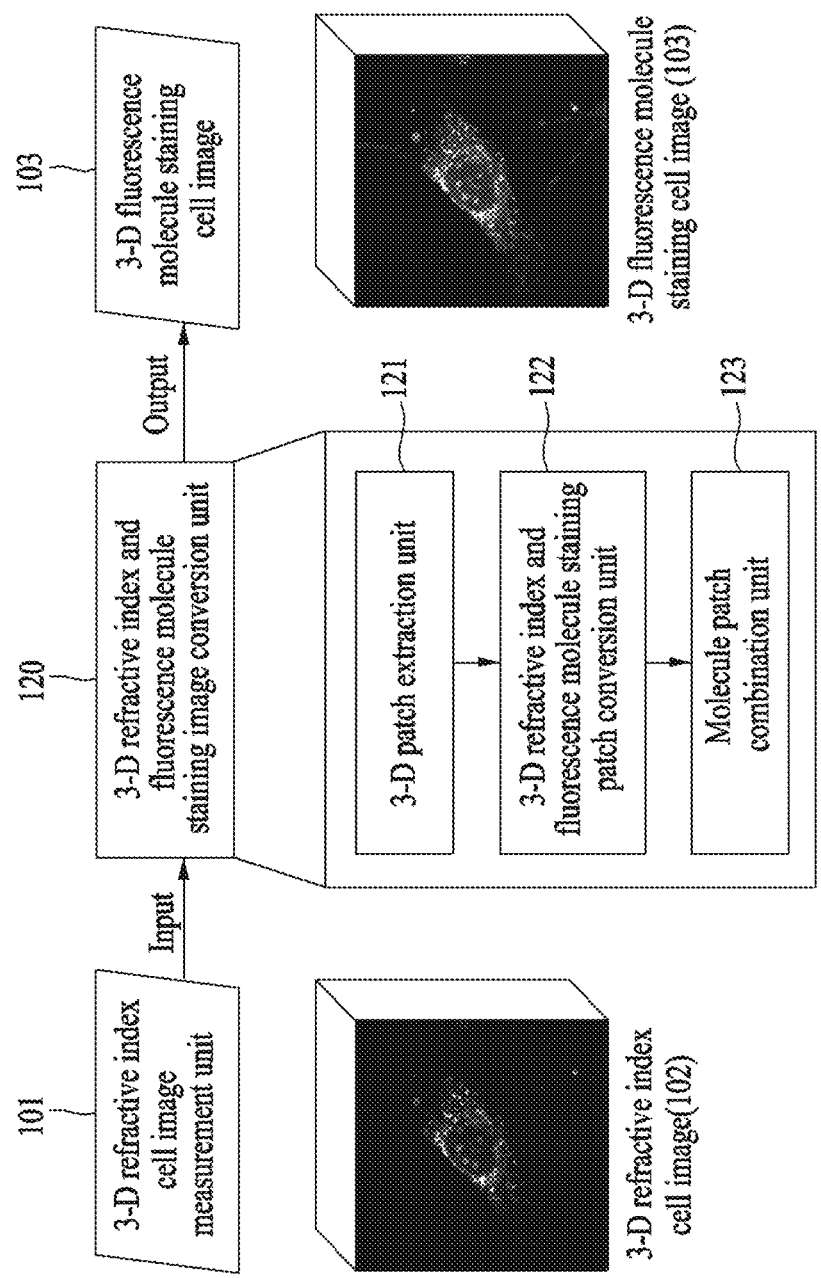
FIG. 4 is a diagram for describing a 3-D refractive index and fluorescence molecule staining image conversion unit according to an embodiment.

FIG. 4 is a diagram for describing the 3-D refractive index and fluorescence molecule staining image conversion unit according to an embodiment.

As illustrated in FIG. 4, for an efficient conversion process, a process of generating a 3-D refractive index image patch by considering 3-D conversion efficiency and a conversion computation environment, converting the 3-D refractive index image patch into a fluorescence molecule staining patch in a patch unit, and merging the fluorescence molecule staining patches may be performed. In this case, a 3-D refractive index cell image 102 is a 3-D refractive index cell image of the entire monitoring area generated using the aforementioned method.

More specifically, the 3-D refractive index and fluorescence molecule staining image conversion unit 120 may include a 3-D patch extraction unit 121, a 3-D refractive index and fluorescence molecule staining patch conversion unit 122, and a molecule patch combination unit 123. The 3-D patch extraction unit 121 may generate the 3-D refractive index image patch of a cell. The 3-D refractive index and fluorescence molecule staining patch conversion unit 122 may convert the 3-D refractive index image patch into a 3-D fluorescence molecule staining image patch 103a based on a deep learning algorithm. Furthermore, the molecule patch combination unit 123 may merge the converted 3-D fluorescence molecule staining image patches 103a into a single image.

In this case, the 3-D refractive index and fluorescence molecule staining image conversion unit 120 may input a measured value of the 3-D refractive index image to the deep learning algorithm, and may output the 3-D fluorescence molecule staining cell image 103 of the cell.

Figure 5:
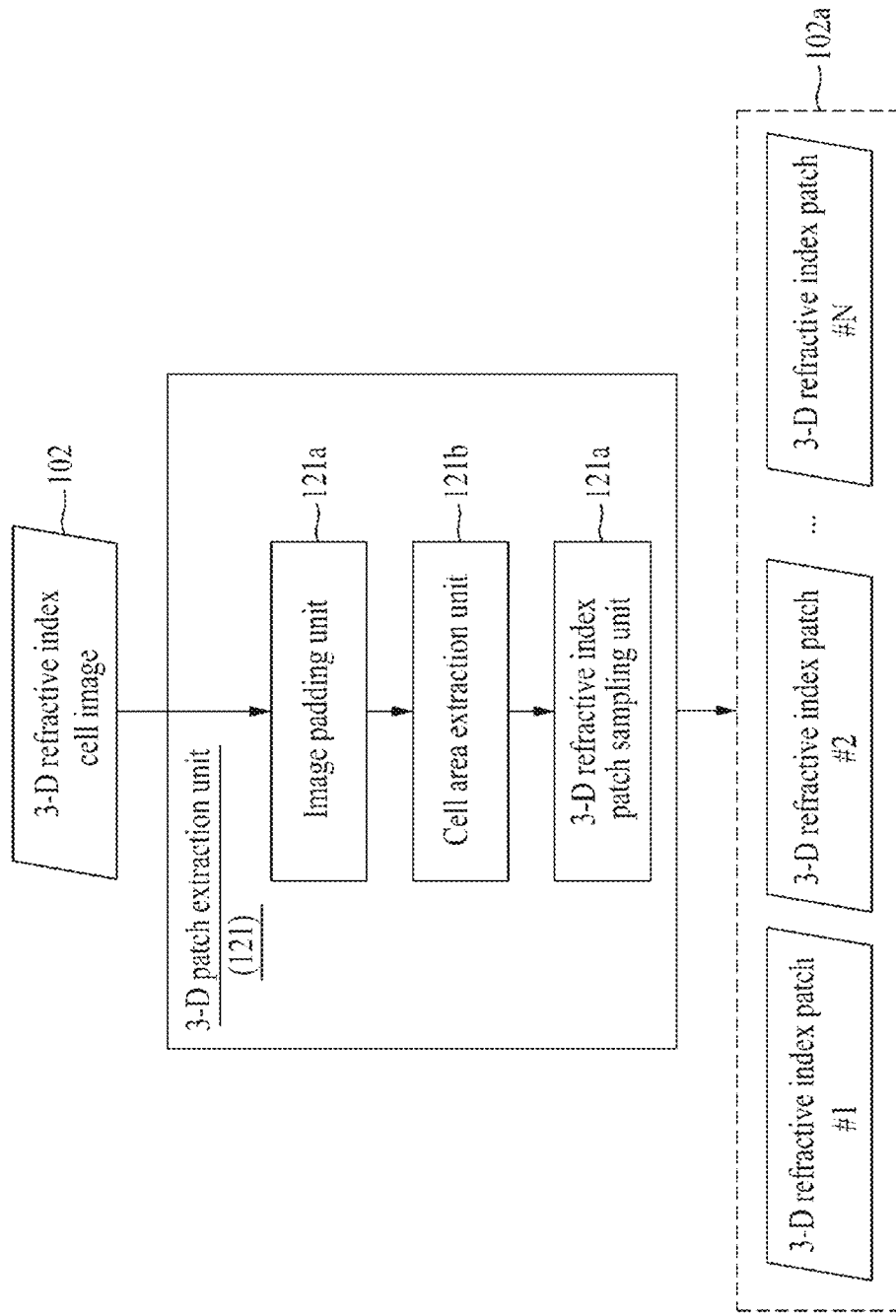
FIG. 5 is a diagram for describing a 3-D patch extraction unit according to an embodiment.

FIG. 5 is a diagram for describing the 3-D patch extraction unit according to an embodiment.

Referring to FIG. 5, according to embodiments, a 3-D refractive index image patch may be converted into a fluorescence molecule staining image in a patch unit. As described above, such a conversion process may be based on a deep learning algorithm. Particularly, a convolutional neural network (CNN) algorithm may be used for the conversion process.

In this case, in order to prevent a loss of outskirt area values occurring in a process of deriving and combining stable results in an image outskirt area, patch sampling may be performed on a cell area after a padding process is performed.

More specifically, the 3-D patch extraction unit 121 may include an image padding unit 121a, a cell area extraction unit 121b, and a 3-D refractive index patch sampling unit 121c.

Figure 6A:
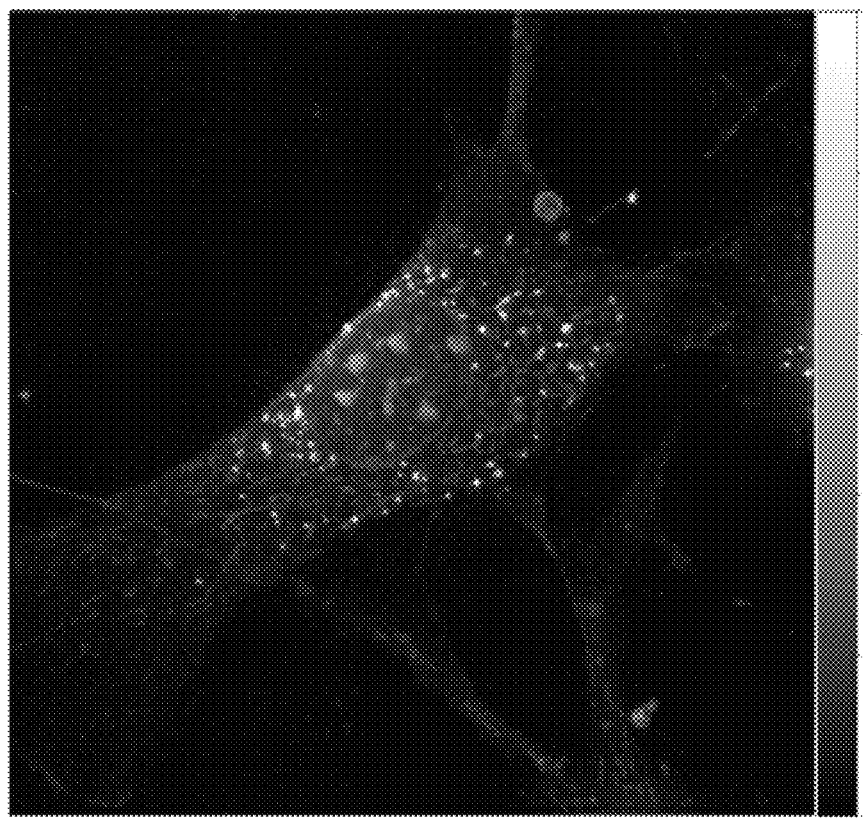
FIG. 6A is a diagram of original image for describing a padding process according to an embodiment.
Figure 6B:
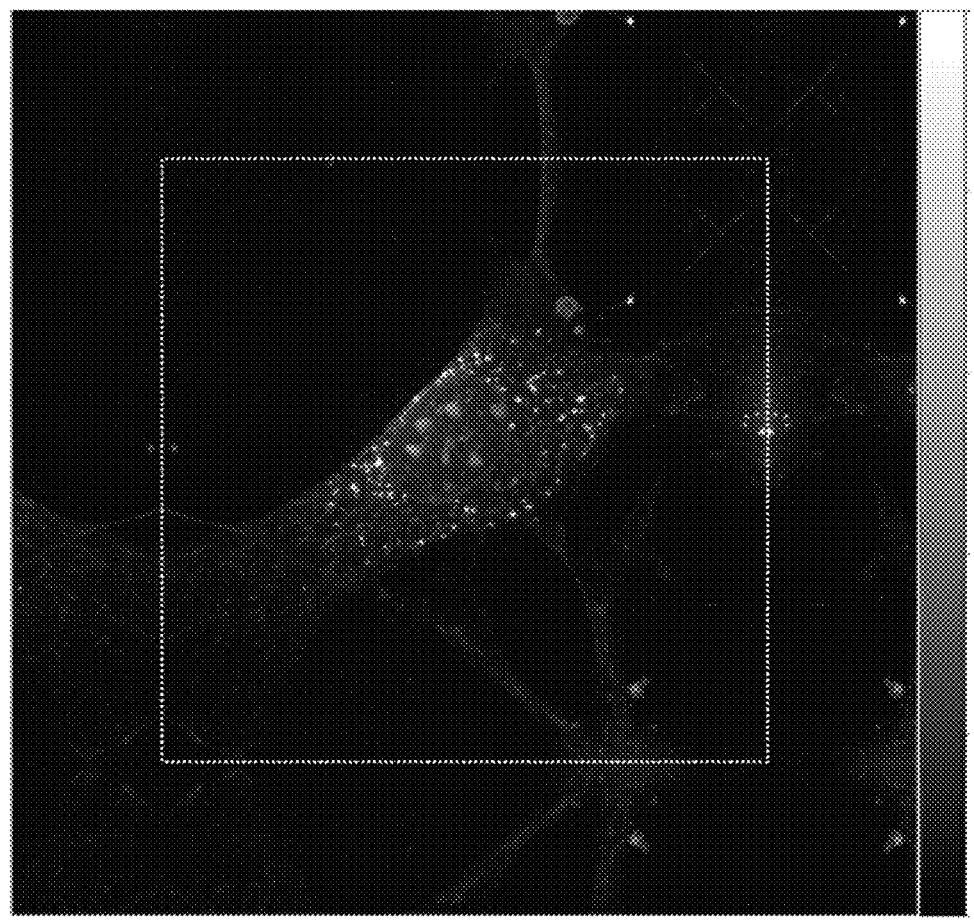
FIG. 6B is a diagram for describing a padding process according to an embodiment.

The image padding unit 121a may perform a padding process in order to prevent a loss of outskirt area values of an image. Prediction reliability of the outskirt part of an image is reduced due to the zero padding effect of a CNN. Furthermore, a value of the outskirt of the image is attenuated because a kernel applied to a patch is a spline function. In order to prevent the two phenomena, padding is performed on the entire image. FIG. 6A is a diagram of original image for describing a padding process according to an embodiment. Furthermore, FIG. 6B is a diagram of padded image for describing a padding process according to an embodiment. As illustrated in FIG. 6A, an original image for describing a padding processor may be shown. As illustrated in FIG. 6B, padding may be performed on the entire image in such a way as to guarantee the continuity of an internal image in proportion to the size of a path which is used for only the outskirt. In this case, the padding may be performed by half the patch size in a patch sampling process to be subsequently performed.

The cell area extraction unit 121b may extract a cell area from an image on which a padding process has been performed.

Figure 7A:
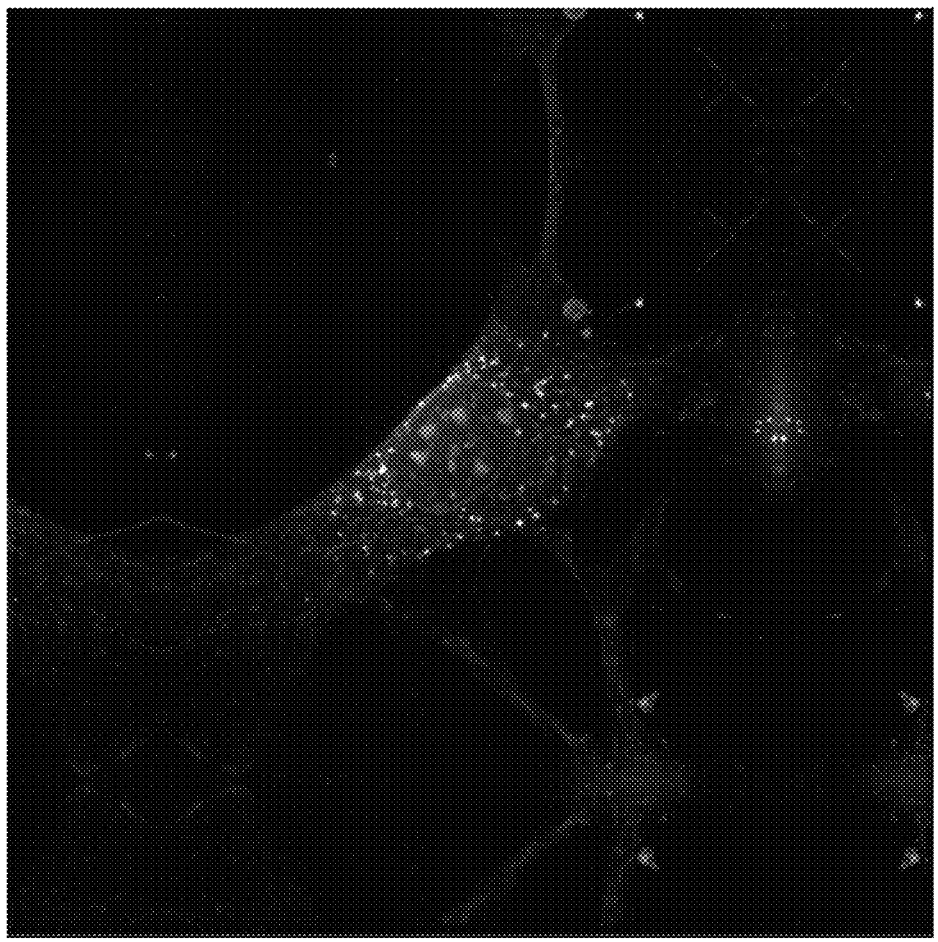
FIG. 7A is a diagram of padded image for describing a patch sampling process according to an embodiment.
Figure 7B:
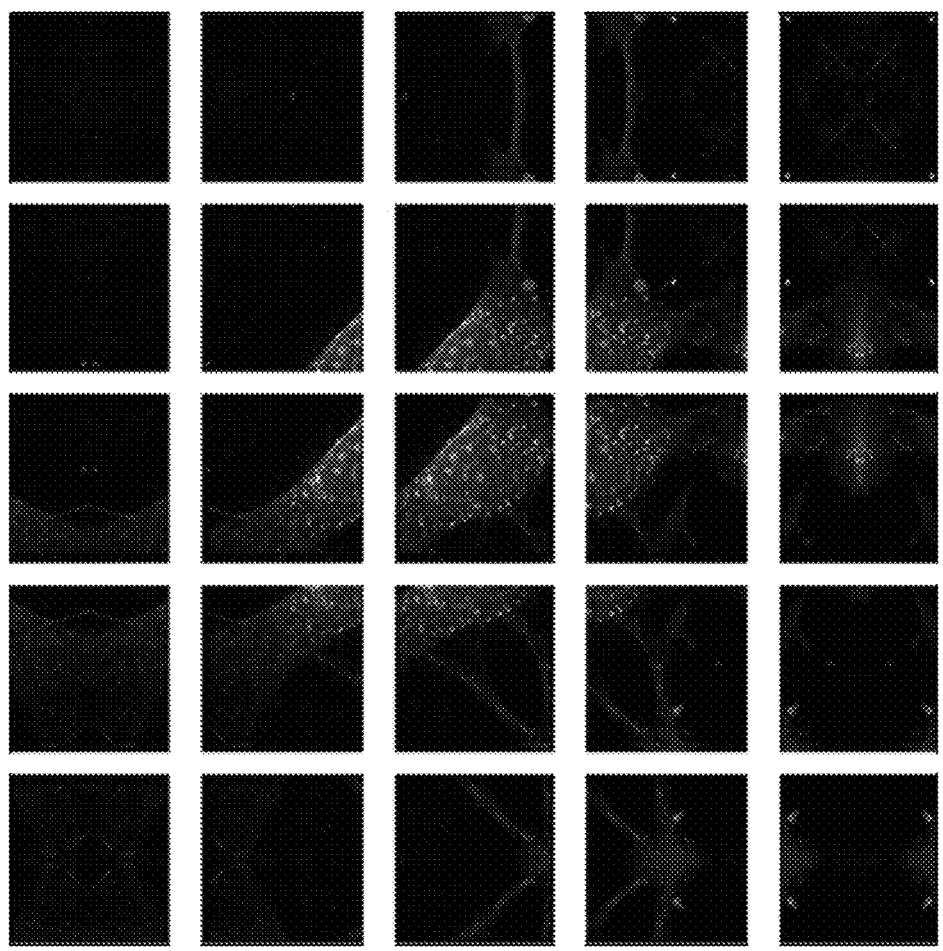
FIG. 7B is a diagram for describing a patch sampling process according to an embodiment.

The 3-D refractive index patch sampling unit 121c may generate the 3-D refractive index image patch of a cell by sampling a patch in the cell area of a padded image. FIG. 7A is a diagram of padded image for describing a patch sampling process according to an embodiment. As illustrated in FIG. 7A, a padded image for describing a patch sampling processor may be shown. Furthermore, FIG. 7B is a diagram for describing a patch sampling process according to an embodiment. There is a difficulty in training the entire image using a CNN due to a limited GPU memory. For this reason, as illustrated in FIG. 7B, a patch may be sampled from a padded image. In this case, a patch sampling interval may be half the patch size in order to effectively remove a zero padding effect and enhance an ensemble effect.

Figure 8:
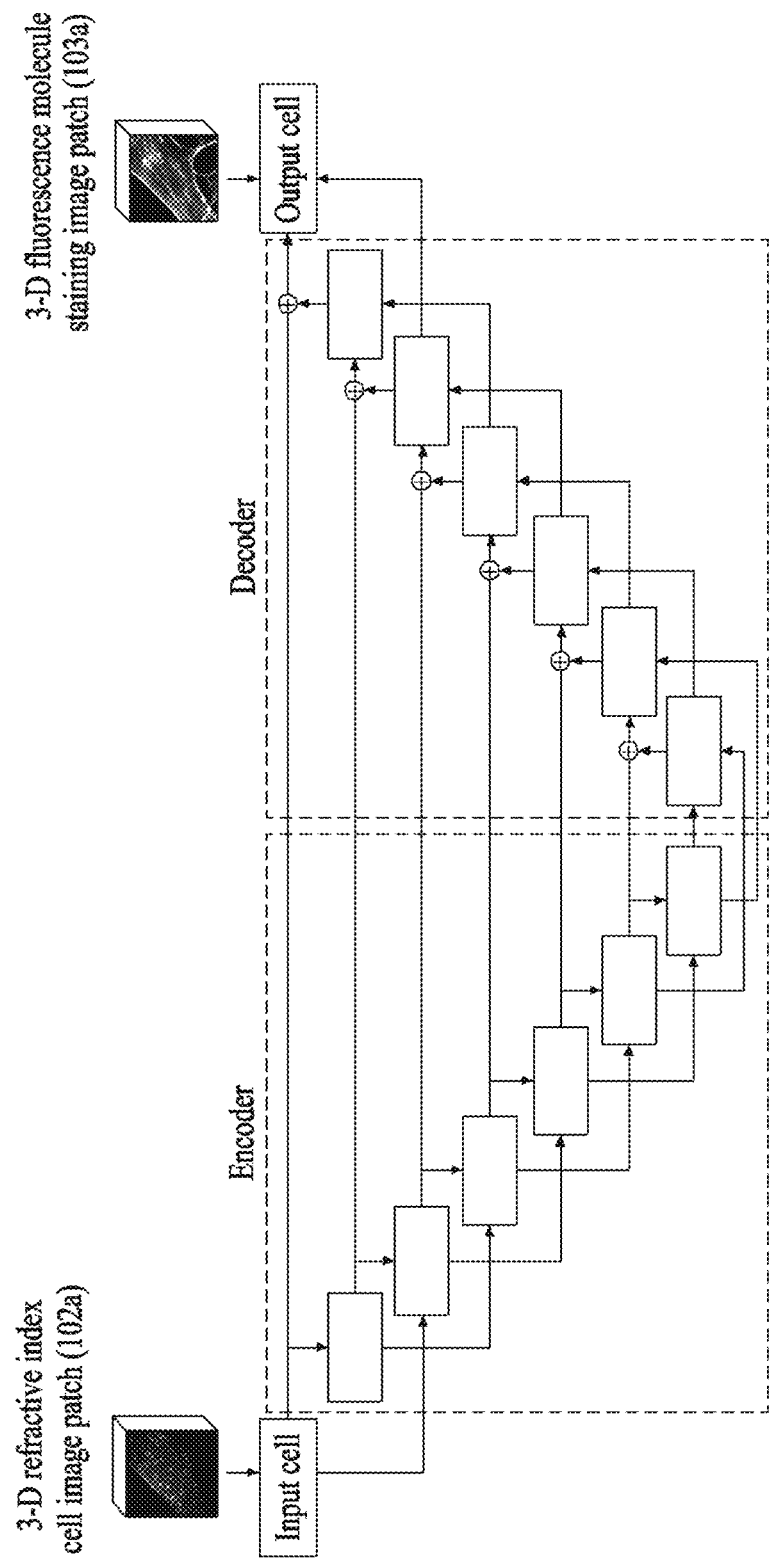
FIG. 8 is a diagram for describing a 3-D refractive index and fluorescence molecule staining patch conversion unit based on a deep learning algorithm according to an embodiment.

FIG. 8 is a diagram for describing the 3-D refractive index and fluorescence molecule staining patch conversion unit based on a deep learning algorithm according to an embodiment.

Referring to FIG. 8, refractive index images of cells may be measured using the aforementioned method, and the 3-D refractive index image patch of a monitored cell may be generated. In this case, each patch may be converted into a molecular image using a trained deep learning model.

More specifically, the 3-D refractive index and fluorescence molecule staining patch conversion unit 122 may convert the 3-D refractive index image patch of each cell into a 3-D fluorescence molecule staining image patch 103a using a CNN trained based on 3-D refractive index information. In this case, information input to the deep learning algorithm is 3-D refractive index information of each cell. A conversion value obtained as a result is molecular label 3-D image information corresponding to an input patch.

Figure 9:
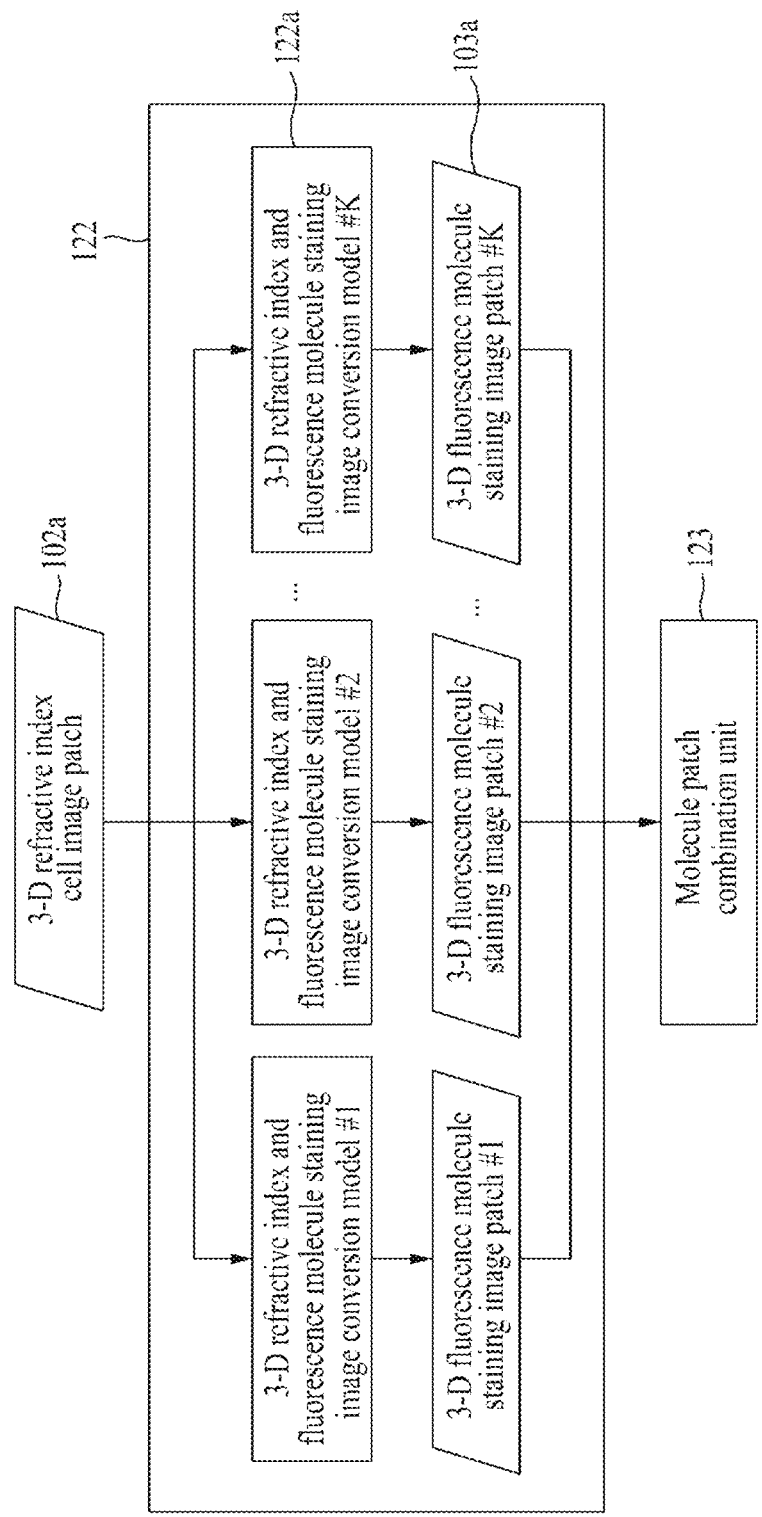
FIG. 9 is a diagram for describing a method of adopting a conversion model suitable for each of pieces of label information according to an embodiment.

FIG. 9 is a diagram for describing a method of adopting a conversion model suitable for each of pieces of label information according to an embodiment. Furthermore, FIG. 10 is a diagram for describing a method of deriving several pieces of molecular label information at a time according to an embodiment.

Figure 10:
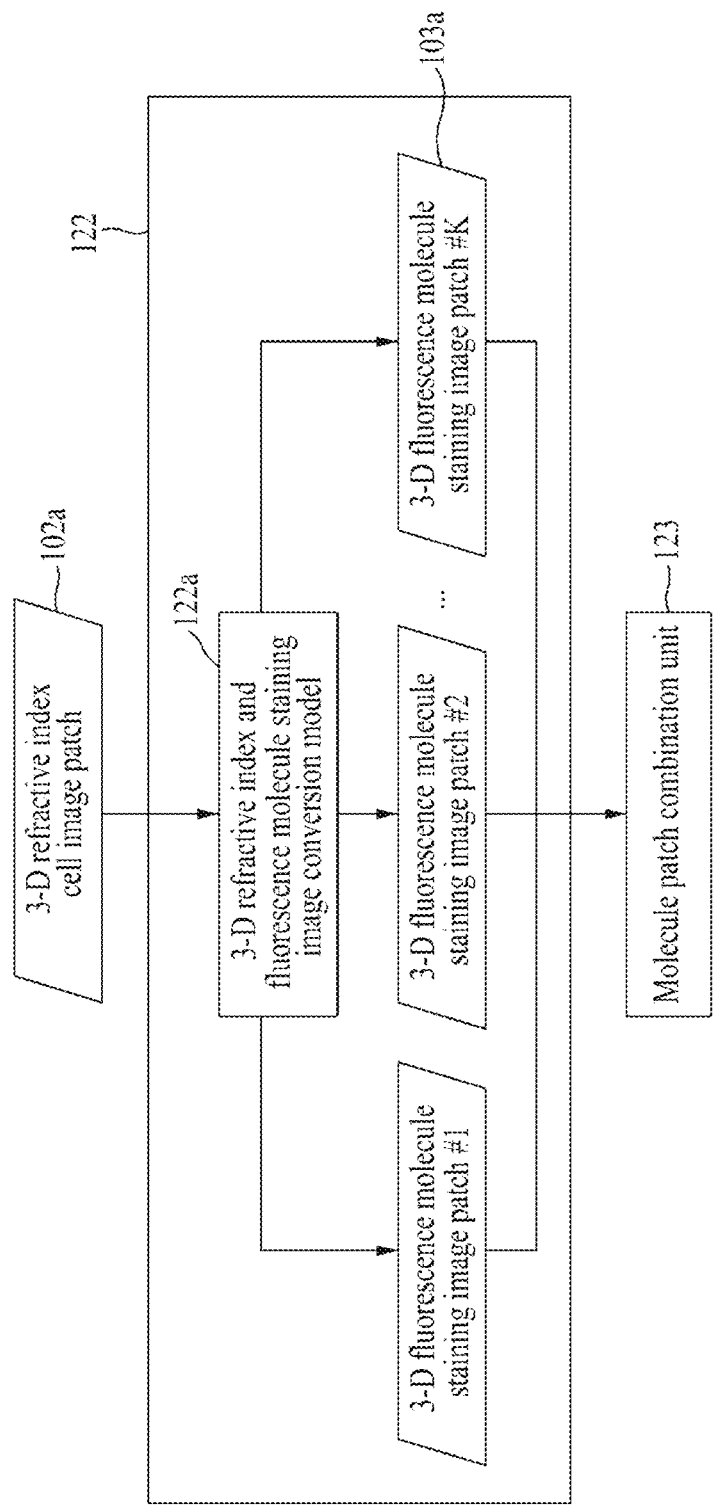
FIG. 10 is a diagram for describing a method of deriving several pieces of molecular label information at a time according to an embodiment.

Particularly, if the number of pieces of molecular label information is one or more, the conversion model can support both a method of adopting a conversion model suitable for each piece of label information, as illustrated in FIG. 9, and a method of deriving several pieces of molecular label information at a time using a single deep learning model as illustrated in FIG. 10.

Figure 11:
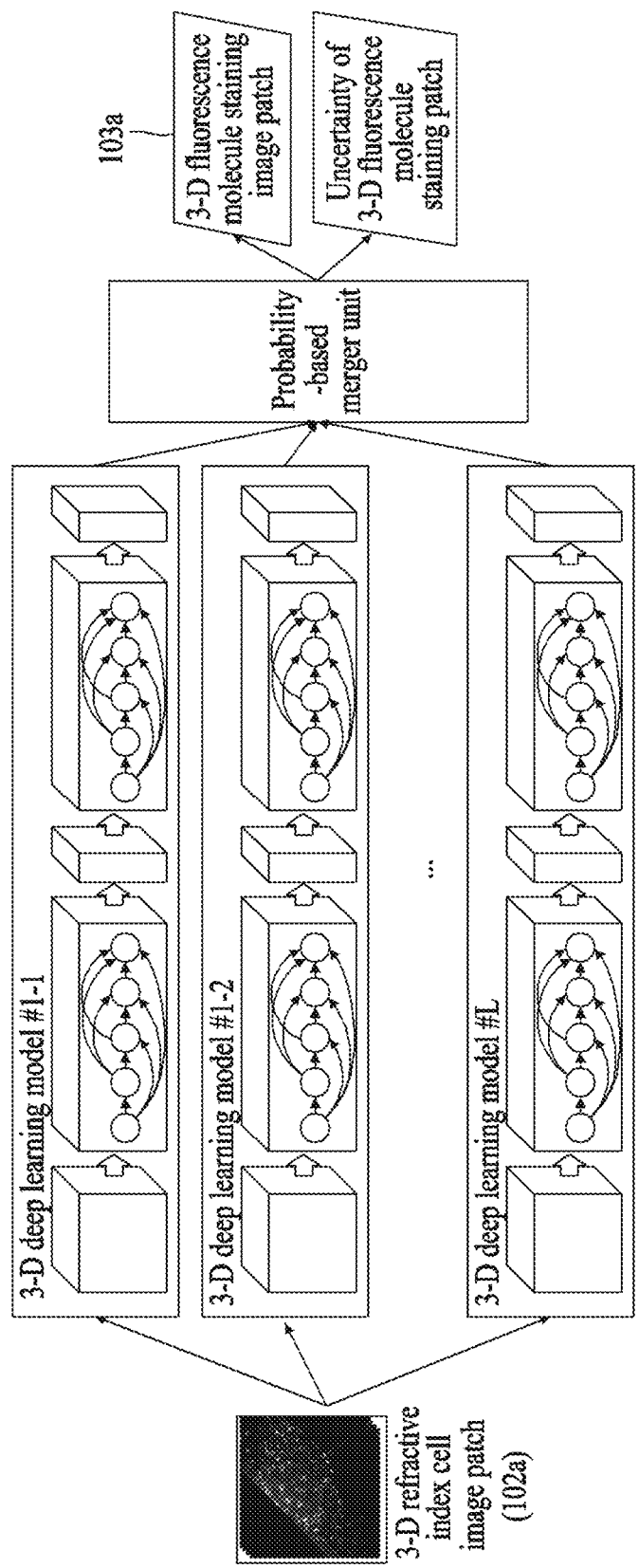
FIG. 11 is a diagram illustrating a deep learning-based model according to an embodiment.

FIG. 11 may illustrate a deep learning-based model according to an embodiment. Furthermore, FIG. 12 is a diagram for describing a 3-D refractive index image patch according to an embodiment.

Referring to FIG. 11, the 3-D refractive index and fluorescence molecule staining image conversion model 122a may use a deep learning algorithm based on measured 3-D refractive index information. In this case, a neural network algorithm, that is, information input to the deep learning algorithm is each 3-D refractive index image patch. Information obtained as a result is 3-D fluorescence molecule staining patch information. In order to maintain stable prediction performance, one or more 3-D refractive index and fluorescence molecule staining image conversion models 122a based on a deep learning algorithm may be trained. Corresponding results may be statistically converged in a probability-based convergence unit, and a 3-D fluorescence molecule staining patch and 3-D fluorescence molecule staining patch uncertainty may be checked.

Figure 12:
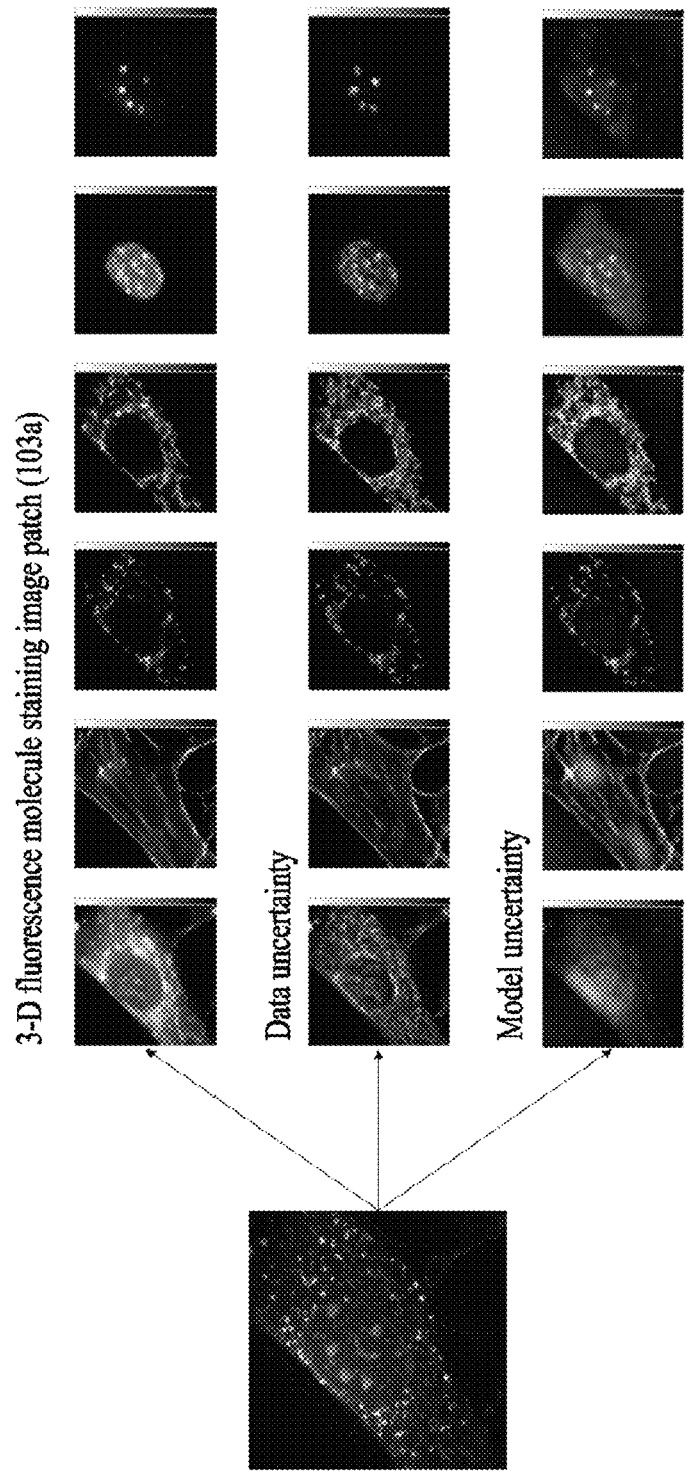
FIG. 12 is a diagram for describing a 3-D refractive index image patch according to an embodiment.

As illustrated in FIG. 12, the model used in the present embodiment can show a more accurate conversion value by also providing uncertainty attributable to insufficient data and insufficient model performance based on values obtained from several models without being based on only a conversion value.

Figure 13A:
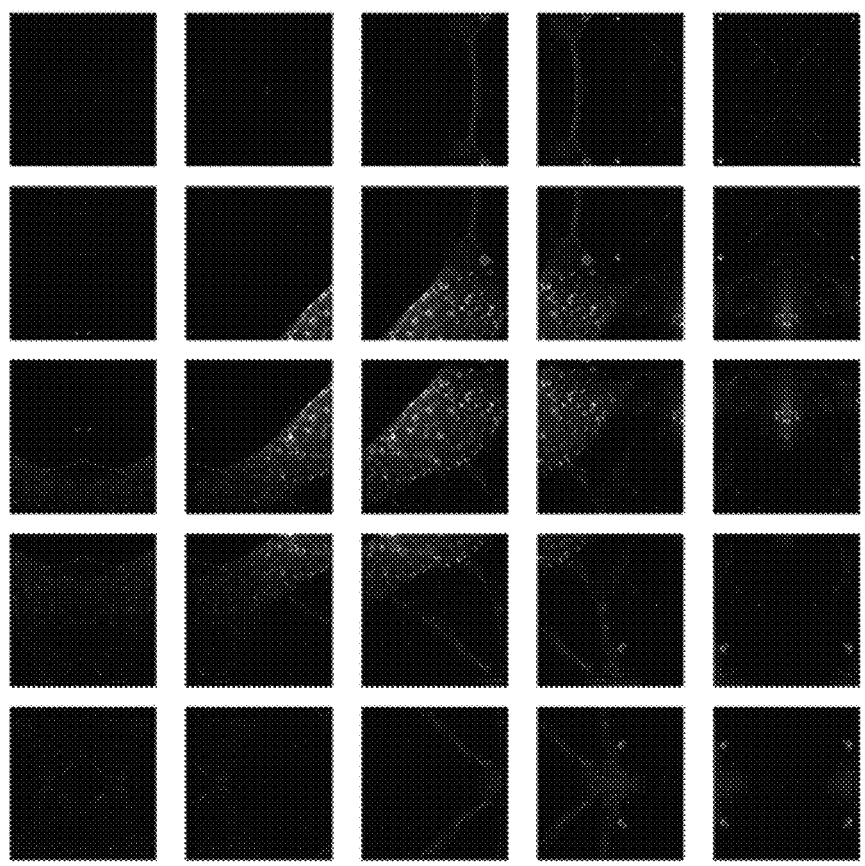
FIG. 13A illustrates the each 3-D refractive index image patch.
Figure 13B:
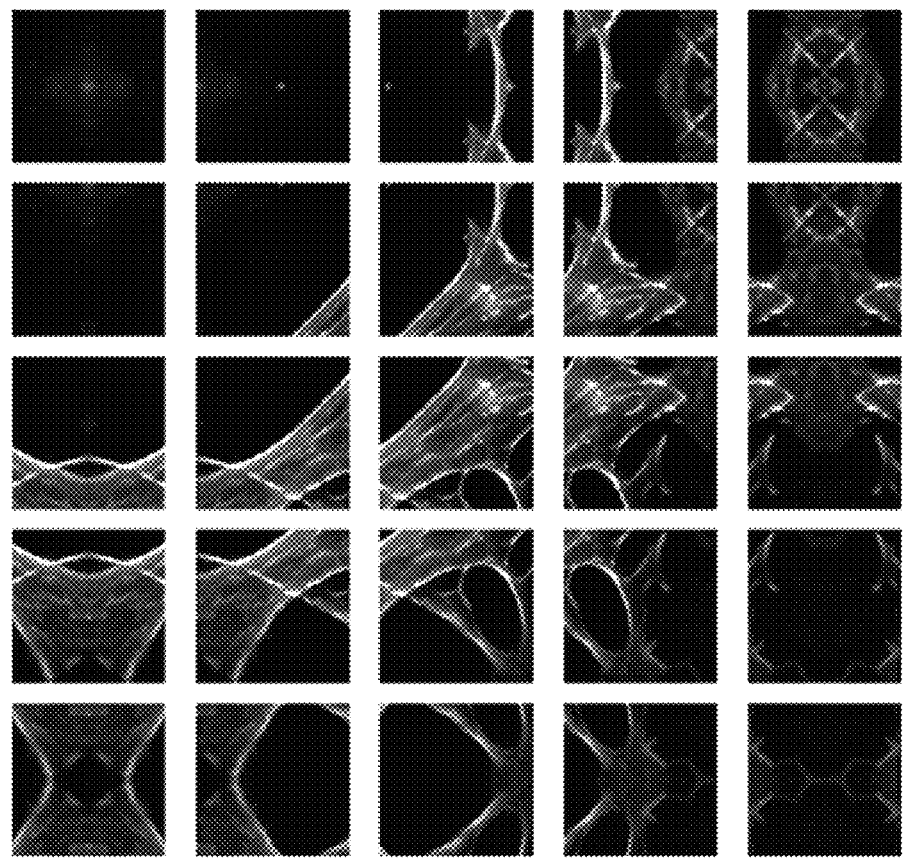
FIG. 13B is a diagram illustrating an example of a converted image patch according to an embodiment.

FIG. 13A is a diagram illustrating an example of a converted image patch according to an embodiment. Furthermore, FIG. 13B is a diagram illustrating an example of a converted image patch according to an embodiment.

FIG. 13A illustrates the each 3-D refractive index image patch. Furthermore, FIG. 13B illustrates an example of image patches converted through the aforementioned process. More specifically, FIG. 13B illustrates an example of images converted from 3-D refractive index image patches into 3-D fluorescence molecule staining image patches 103a.

Figure 14:
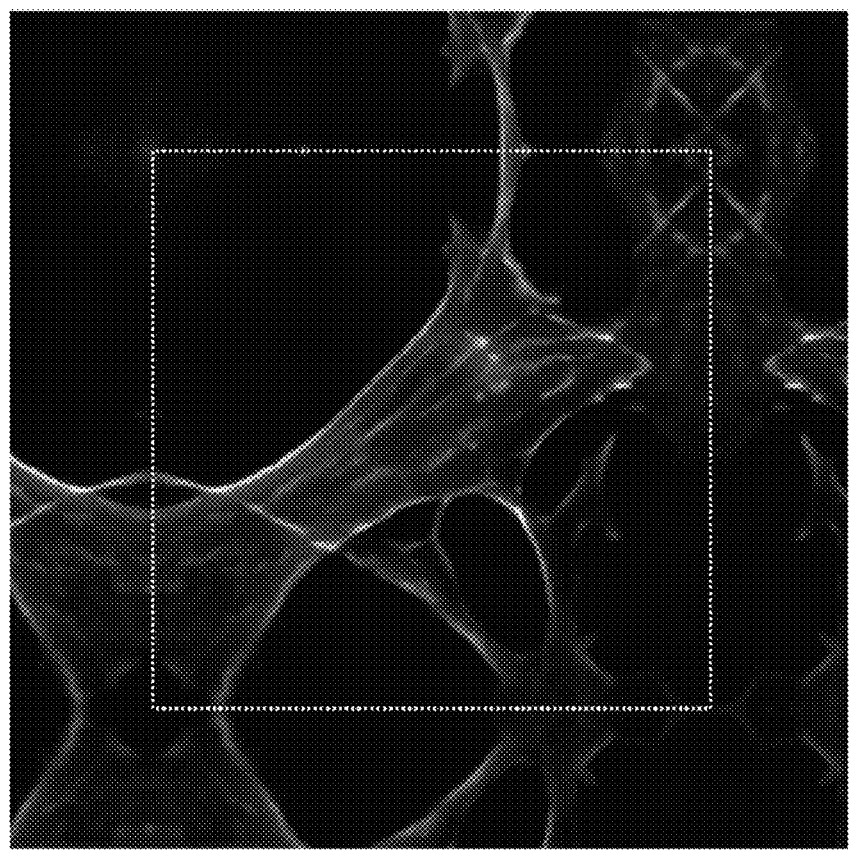
FIG. 14 is a diagram for describing the merger of 3-D molecular image patches according to an embodiment.

FIG. 14 is a diagram for describing the merger of 3-D molecular image patches according to an embodiment.

As illustrated in FIG. 14, the molecule patch combination unit 123 may merge converted 3-D fluorescence molecule staining image patches 103a into a single image. In this case, regarding an overlapped area, in order to guarantee the continuity of a reconstructed image, a linear/non-linear weight according to a distance from the middle of a patch is multiplied.

Figure 15:
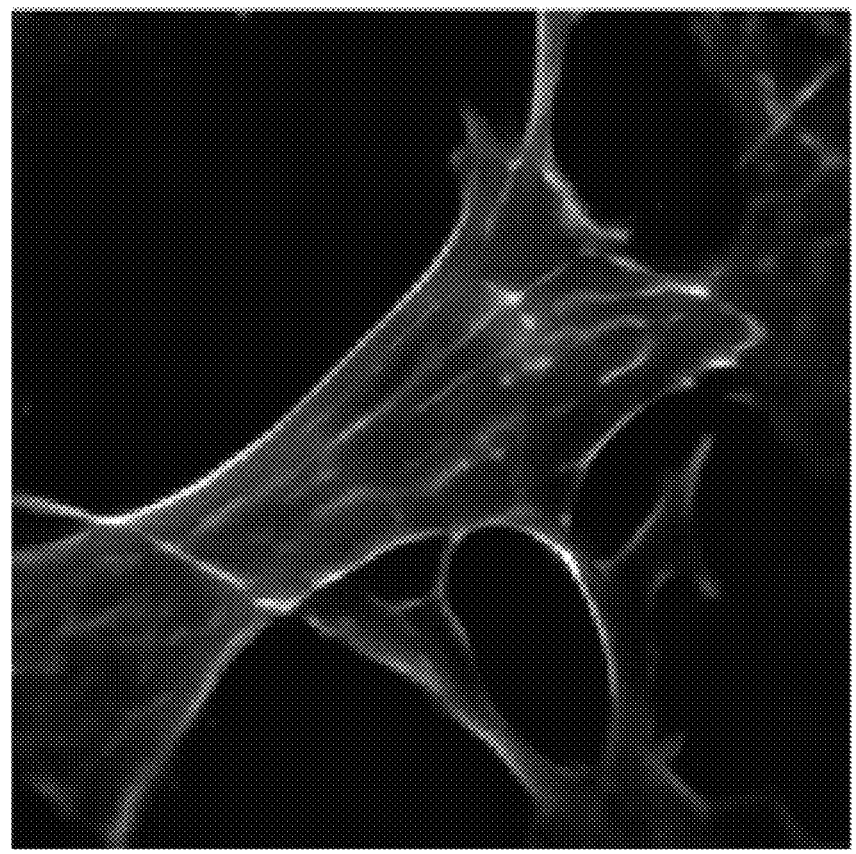
FIG. 15 is a diagram for describing the removal of a padding area according to an embodiment.

FIG. 15 is a diagram for describing the removal of a padding area according to an embodiment.

As illustrated in FIG. 15, a padded area may be removed. Accordingly, a 3-D image for one molecular label may be finally formed.

In other words, in order to guarantee the continuity of an image reconstructed for an overlapped area, the molecule patch combination unit 123 may add and multiply a linear or non-linear weight according to a distance from the middle of a patch, may remove a padding area, and may then finally generate a 3-D fluorescence molecule staining cell image 103 of a cell for one molecular label.

Figure 16:
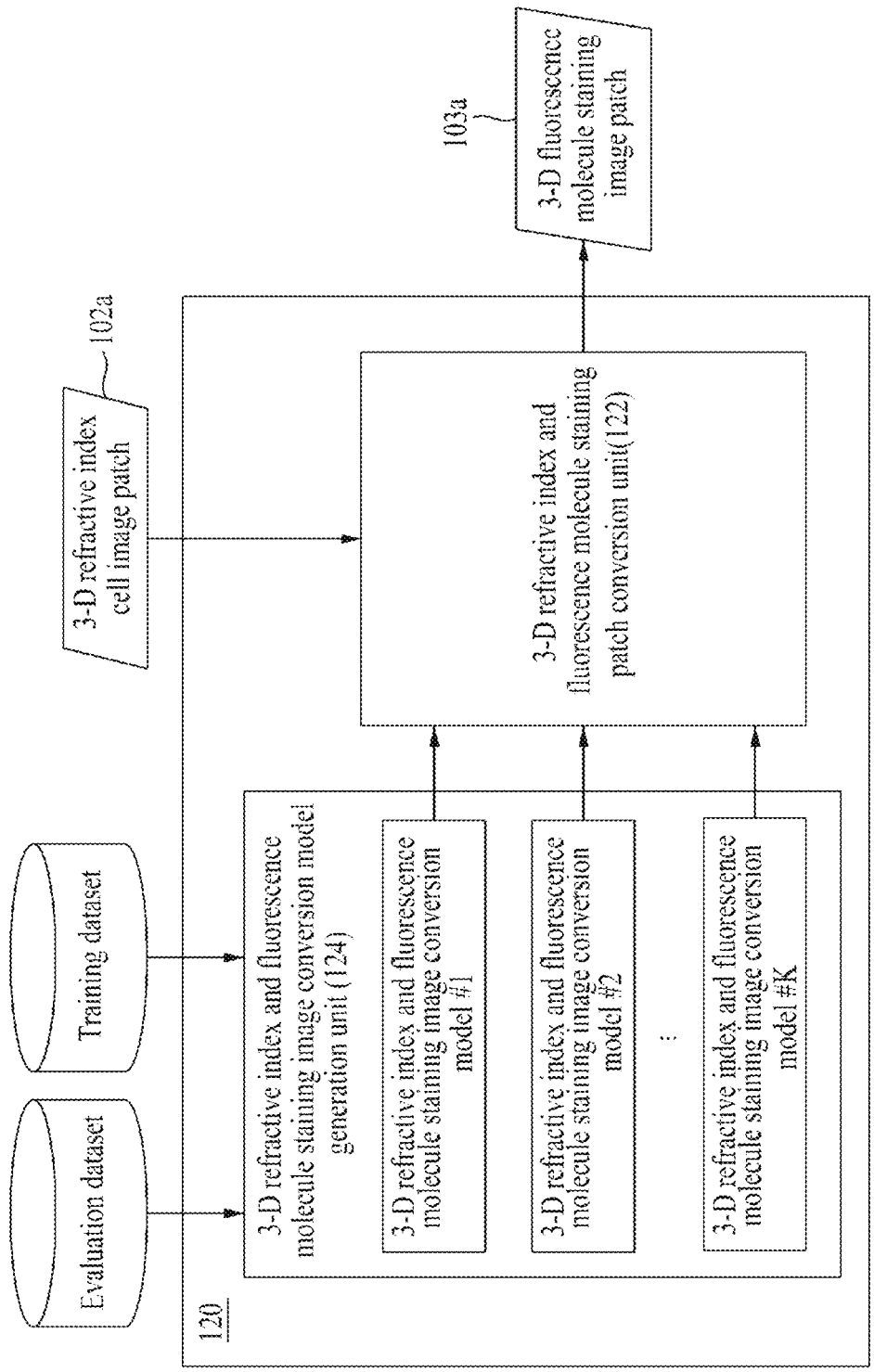
FIG. 16 is a diagram for describing a 3-D refractive index and fluorescence molecule staining image conversion model according to an embodiment.

FIG. 16 is a diagram for describing a 3-D refractive index and fluorescence molecule staining image conversion model according to an embodiment.

Referring to FIG. 16, a 3-D refractive index image corresponding to a cell having an already specific molecular label may be measured. In this case, after a large number of samples (>50) are measured for each molecular label, a conversion model may be constructed using a deep learning algorithm.

In other words, the 3-D refractive index and fluorescence molecule staining image conversion model generation unit 124 may measure the preset number of samples or more for each molecular label using an evaluation data set and a training data set, and may construct a 3-D refractive index and fluorescence molecule staining image conversion model 122a using a deep learning algorithm.

Accordingly, the 3-D refractive index and fluorescence molecule staining image conversion unit 120 may measure a 3-D refractive index image corresponding to a cell having a specific molecular label through the 3-D refractive index and fluorescence molecule staining image conversion model 122a, and may generate the 3-D fluorescence molecule staining cell image 103 of the cell.

Figure 17:
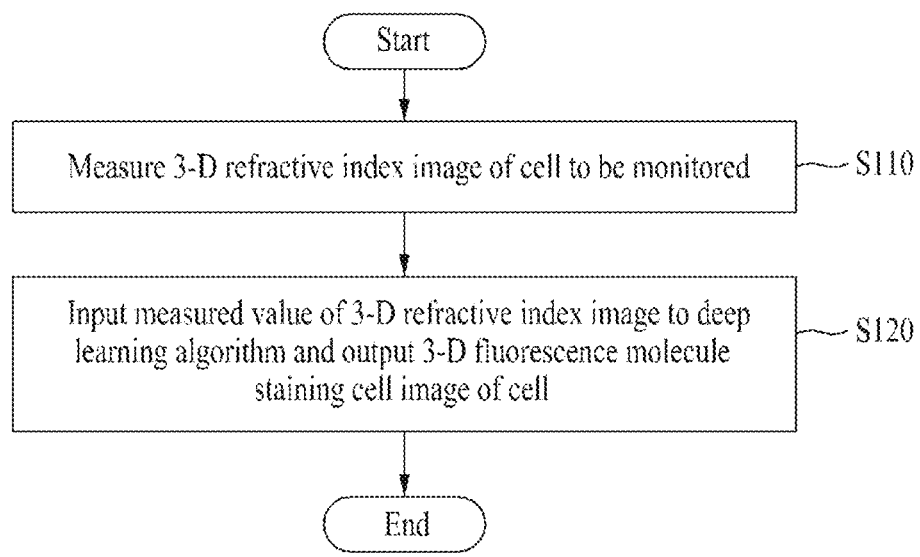
FIG. 17 is a flowchart for describing a method of generating a 3-D molecular image based on a label-free method using a 3-D refractive index image and deep learning according to an embodiment.

FIG. 17 is a flowchart for describing a method of generating a 3-D molecular image based on a label-free method using a 3-D refractive index image and deep learning according to an embodiment.

Referring to FIG. 17, the method of generating a 3-D molecular image based on a label-free method using a 3-D refractive index image and deep learning according to an embodiment may include step S110 of measuring a 3-D refractive index image of a cell to be monitored, and step S120 of inputting a measured value of the 3-D refractive index image to a deep learning algorithm and outputting a 3-D fluorescence molecule staining cell image of the cell.

Furthermore, before the 3-D fluorescence molecule staining cell image of the cell is output, step S120 may include the step of measuring the preset number of samples or more for each molecular label and constructing a 3-D refractive index and a fluorescence molecule staining image conversion model using a deep learning algorithm.

Each of the steps of the method of generating a 3-D molecular image based on a label-free method using a 3-D refractive index image and deep learning according to an embodiment is described below.

The method of generating a 3-D molecular image based on a label-free method using a 3-D refractive index image and deep learning according to an embodiment may be described more specifically using the apparatus 100 for generating a 3-D molecular image based on a label-free method using a 3-D refractive index image and deep learning according to an embodiment with reference to FIGS. 1 to 16.

In step S110, the 3-D refractive index cell image measurement unit 110 may measure a 3-D refractive index image of a cell to be monitored. For example, the 3-D refractive index cell image measurement unit 110 may capture the 3-D refractive index image in a form in which the cell to be monitored is placed or painted on a slide.

In step S120, the 3-D refractive index and fluorescence molecule staining image conversion unit 120 may input a measured value of the 3-D refractive index image to a deep learning algorithm, and may output a 3-D fluorescence molecule staining cell image of the cell.

The 3-D refractive index and fluorescence molecule staining image conversion unit 120 may generate the 3-D refractive index image patch of the cell, may convert the 3-D refractive index image patch into a 3-D fluorescence molecule staining image patch based on the deep learning algorithm, and may merge the converted 3-D fluorescence molecule staining image patches into a single image.

Furthermore, before the 3-D fluorescence molecule staining cell image of the cell is output, after the preset number of samples or more is measured for each molecular label, the 3-D refractive index and fluorescence molecule staining image conversion model 122a may be constructed using the deep learning algorithm. Accordingly, a 3-D fluorescence molecule staining cell image of the cell can be generated by measuring a 3-D refractive index image corresponding to a cell having a specific molecular label through the 3-D refractive index and fluorescence molecule staining image conversion model 122a.

The method of generating a 3-D molecular image based on a label-free method using a 3-D refractive index image and deep learning according to an embodiment overlaps the description of the apparatus 100 for generating a 3-D molecular image based on a label-free method using a 3-D refractive index image and deep learning according to an embodiment, and the redundant description is omitted.

As described above, according to the embodiments, there can be provided the method of rapidly generating a molecular microscope image using the 3-D refractive index measurement of a cell and a deep learning algorithm without a process, such as dyeing or labeling. According to the embodiments, a cell can be rapidly analyzed without affecting the cell because both the morphologic features and physical/chemical characteristics of the cell can be extracted without using dyeing and labeling. Furthermore, consistent and stable analysis information can be extracted because a cell is not affected by the inconsistence of dyeing and labeling. Accordingly, information that is not monitored in a conventional technology can be derived.

The aforementioned apparatus may be implemented as a hardware component, a software component and/or a combination of them. For example, the apparatus and components described in the embodiments may be implemented using one or more general-purpose computers or special-purpose computers, for example, a processor, a controller, an arithmetic logic unit (ALU), a digital signal processor, a microcomputer, a field programmable array (FPA), a programmable logic unit (PLU), a microprocessor or any other device capable of executing or responding to an instruction. The processing apparatus may perform an operating system (OS) and one or more software applications executed on the OS. Furthermore, the processing apparatus may access, store, manipulate, process and generate data in response to the execution of software. For convenience of understanding, one processing apparatus has been illustrated as being used, but a person having ordinary skill in the art may understand that the processing apparatus may include a plurality of processing elements and/or a plurality of types of processing elements. For example, the processing apparatus may include a plurality of processors or a single processor and a single controller. Furthermore, other processing configurations, such as a parallel processor, are also possible.

Software may include a computer program, code, an instruction or a combination of one or more of them and may configure the processor so that it operates as desired or may instruct the processor independently or collectively.

The software and/or data may be embodied in a machine, component, physical device, virtual equipment or computer storage medium or device of any type or a transmitted signal wave permanently or temporarily in order to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure solely or in combination. The program instruction recorded on the recording medium may have been specially designed and configured for the embodiment or may have been known to those skilled in the computer software. The computer-readable recording medium includes magnetic media such as a hard disk, a floppy disk and a magnetic tape, optical media such as a CD-ROM and a DVD, magneto-optical media such as a floptical disk, and hardware devices specially configured to store and execute program instructions, such as ROM, RAM, and flash memory, for example. Examples of the program instruction may include high-level language code executable by a computer using an interpreter in addition to machine-language code, such as code written by a compiler.

As described above, although the embodiments have been described in connection with the limited embodiments and drawings, those skilled in the art may modify and change the embodiments in various ways from the description. For example, proper results may be achieved although the above descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and equivalents of the claims belong to the scope of the claims.

According to the embodiments, there can be provided the method and apparatus for generating a 3-D molecular image based on a label-free method using a 3-D refractive index image and deep learning, wherein the morphologic features of a cell are measured using a 3-D refractive index a microscope without dyeing or labeling and a 3-D molecular microscope image is generated by applying a deep learning algorithm in order to predict a fluorescence label image for showing the physical-chemical characteristics of the cell based on the morphologic features.

What is claimed is:

1. An apparatus for generating a three-dimensional (3-D) molecular image based on a label-free method using a 3-D refractive index image and deep learning, the apparatus comprising:
    a 3-D refractive index cell image measurement unit configured to measure a 3-D refractive index image of a label-free cell to be monitored; and
    a 3-D refractive index and fluorescence molecule staining image conversion unit configured to input a measured value of the 3-D refractive index image to a deep learning algorithm and to output a 3-D fluorescence molecule staining cell image of the label-free cell,
    wherein the deep learning algorithm unit does not receive fluorescent image data of the cell as input.

2. The apparatus of claim 1, wherein the 3-D refractive index cell image measurement unit captures the 3-D refractive index image in a form in which the cell to be monitored is placed or painted on a slide.

3. The apparatus of claim 1, wherein the 3-D refractive index cell image measurement unit comprises:
    a 3-D image patch photographing unit configured to capture a 3-D refractive index image capable of being captured at a time when a monitoring area of the cell is greater than an area capable of being photographed at a time; and
    an image patch combination unit configured to generate a 3-D refractive index slide image by connecting the 3-D refractive index images each captured at a time.

4. The apparatus of claim 1, wherein the 3-D refractive index and fluorescence molecule staining image conversion unit comprises:
    a 3-D patch extraction unit configured to generate a 3-D refractive index image patch of the cell;
    a 3-D refractive index and fluorescence molecule staining patch conversion unit configured to convert the 3-D refractive index image patch into a 3-D molecular image patch based on the deep learning algorithm; and
    a molecule patch combination unit configured to merge the converted 3-D molecular image patches into a single image.

5. The apparatus of claim 4, wherein the 3-D patch extraction unit comprises:
    an image padding unit configured to perform a padding process in order to prevent a loss of outskirt area values of an image;
    a cell area extraction unit configured to extract a cell area from an image on which the padding process has been performed; and
    a 3-D refractive index patch sampling unit configured to generate the 3-D refractive index image patch of the cell by sampling a patch in the cell area of the padded image.

6. The apparatus of claim 4, wherein the 3-D refractive index and fluorescence molecule staining patch conversion unit converts the 3-D refractive index image patch of each cell into the 3-D molecular image patch using a convolutional neural network (CNN) trained based on 3-D refractive index information.

7. The apparatus of claim 4, wherein the molecule patch combination unit multiplies and adds a linear or non-linear weight according to a distance from a middle of the patch in order to guarantee a continuity of an image reconstructed for an overlapped area, removes a padding area, and finally generates the 3-D fluorescence molecule staining cell image of the cell for one molecular label.

8. The apparatus of claim 1, wherein:
    the 3-D refractive index and fluorescence molecule staining image conversion unit comprises a 3-D refractive index and fluorescence molecule staining image conversion model generation unit configured to measure a preset number of samples or more for each molecular label and to construct a 3-D refractive index and fluorescence molecule staining image conversion model using the deep learning algorithm, and
    the 3-D fluorescence molecule staining cell image of the cell is generated by measuring a 3-D refractive index image corresponding to a cell having a specific molecular label through the 3-D refractive index and fluorescence molecule staining image conversion model.

9. A method of generating a three-dimensional (3-D) molecular image based on a label-free method using a 3-D refractive index image and deep learning, the method comprising:
    measuring a 3-D refractive index image of a label-free cell to be monitored; and
    inputting a measured value of the 3-D refractive index image to a deep learning algorithm and outputting a 3-D fluorescence molecule staining cell image of the label-free cell,
    wherein the deep learning algorithm unit does not receive fluorescent image data of the cell as input.

10. The method of claim 9, wherein:
    outputting the 3-D fluorescence molecule staining cell image of the cell comprises measuring a preset number of samples or more for each molecular label and constructing a 3-D refractive index and fluorescence molecule staining image conversion model using the deep learning algorithm, and
    the 3-D fluorescence molecule staining cell image of the cell is generated by measuring a 3-D refractive index image corresponding to a cell having a specific molecular label through the 3-D refractive index and fluorescence molecule staining image conversion model.

* * * * *